(12) United States Patent
Feng

(10) Patent No.: US 7,087,150 B2
(45) Date of Patent: Aug. 8, 2006

(54) CHLORAMINE AMPEROMETRIC SENSOR

(75) Inventor: Chang-Dong Feng, Long Beach, CA (US)

(73) Assignee: Rosemount Analytical Inc., Irvine, CA (US)

( * ) Notice: Subject to any disclaimer, the term of this patent is extended or adjusted under 35 U.S.C. 154(b) by 0 days.

(21) Appl. No.: 10/138,359

(22) Filed: May 3, 2002

(65) Prior Publication Data

US 2003/0205465 A1    Nov. 6, 2003

(51) Int. Cl.
*G01N 27/404*    (2006.01)

(52) U.S. Cl. .................... 205/780; 205/780.5; 204/431

(58) Field of Classification Search ................ 204/415, 204/430, 431; 205/778.5, 780, 780.5
See application file for complete search history.

(56) References Cited

U.S. PATENT DOCUMENTS

| | | | |
|---|---|---|---|
| 3,429,796 A | 2/1969 | Lauer | |
| 3,708,412 A * | 1/1973 | Lofgren | ...................... 204/415 |
| 3,755,125 A * | 8/1973 | Shaw et al. | |
| 3,959,087 A | 5/1976 | Morrow | ....................... 204/1 T |
| 4,111,760 A | 9/1978 | Chen et al. | |
| 4,129,479 A | 12/1978 | Morrow | ....................... 204/1 T |
| 4,176,031 A | 11/1979 | Rosenblum | ............... 204/195 R |
| 4,201,634 A * | 5/1980 | Stetter | ....................... 205/780.5 |
| 4,278,507 A | 7/1981 | Derreumaux et al. | ........ 204/1 T |
| 4,322,215 A | 3/1982 | Huber et al. | ............... 23/230 R |
| 4,525,704 A * | 6/1985 | Campbell et al. | |
| 4,756,804 A * | 7/1988 | Driscoll et al. | |
| 4,776,942 A | 10/1988 | Neti et al. | ................... 204/415 |
| 4,822,474 A | 4/1989 | Corrado | ....................... 204/402 |
| 5,030,336 A * | 7/1991 | Koch | ......................... 204/415 |
| 5,302,274 A * | 4/1994 | Tomantschger et al. | |
| 5,693,204 A | 12/1997 | Popp | ........................... 204/409 |
| 5,711,861 A * | 1/1998 | Ward et al. | |
| 5,725,747 A * | 3/1998 | Pinkowski et al. | |
| 5,728,290 A * | 3/1998 | Xie et al. | |
| 5,770,039 A | 6/1998 | Rigney et al. | |
| 5,830,337 A * | 11/1998 | Xu | |
| 5,855,750 A * | 1/1999 | Kiesele | |
| 5,869,342 A | 2/1999 | Stannard et al. | ............... 436/55 |
| 6,423,209 B1 * | 7/2002 | Weber et al. | ................ 205/775 |
| 2001/0032789 A1 | 10/2001 | Babes-Dornea et al. | |

FOREIGN PATENT DOCUMENTS

| | | |
|---|---|---|
| CA | 2 360 599 | 5/2002 |
| DE | 198 47 706 | 4/2000 |
| GB | 858677 | 1/1961 |

(Continued)

OTHER PUBLICATIONS

Toxic Gas CiTiceLs, product catalog and manual, pp. 2-39. Published on or before Jul. 30, 1999.*

(Continued)

*Primary Examiner*—Kaj K. Olsen
(74) *Attorney, Agent, or Firm*—Westman, Champlin & Kelly, P.A.

(57) ABSTRACT

A chloramine amperometric sensor includes a sensor body with an electrolyte disposed inside the sensor body. A membrane is coupled to the sensor body and adapted to pass chloramine therethrough. A reference electrode is disposed in the electrolyte and coupled to a first conductor. A second conductor is coupled to a working electrode that is disposed proximate the membrane. The working electrode is constructed from a noble metal in non-compact form. The non-compact form can be a Gas Diffusion Electrode, which can include metal mesh, carbon paper, carbon cloth, metal/carbon powder loaded on a porous membrane or any combination thereof.

16 Claims, 8 Drawing Sheets

GAS DIFFUSION ELECTRODE (SENSOR 40)

FOREIGN PATENT DOCUMENTS

| | | |
|---|---|---|
| GB | 1569 026 | 6/1980 |
| JP | 01 041853 | 2/1989 |
| WO | WO 97/42497 | 11/1997 |

OTHER PUBLICATIONS

"Chlorine Residual Analyzer Series 1770," Severn Trent Services, pp. 1-4 (2000).

"Chlorine Residual Analyzer Series 1870E," Severn Trent Services, pp. 1-4 (2000).

"E-TEK Catalogue, C. Noble Metal Catalysts on Carbon," downloaded from http://www.etek-inc.com/C.html, 7 pages (Aug. 14, 2001).

"E-TEK Catalogue, C. Noble Metal Catalysts on Carbon," downloaded from http://www.eteck-inc.com/C1-7.html, 5 pages (May 24, 2001).

"E-TEK Catalogue, A-5 Sensor Electrodes (ESE)," downloaded from http://www.etek-inc.com/A5.html, 2 pages (Aug. 14, 2001).

"E-TEK Catalogue, A-1 Carbon Cloth Electrode (ECC)," downloaded from http://www.etek-inc.com/A1.html, 2 pages (Aug. 15, 2001).

"E-TEK Catalogue, A. Gas Diffusion Electrodes & Services," downloaded from http://www.etek-inc.com/A.html, 2 pages (Aug. 14, 2001).

"Applications. What is a Gas Diffusion Electrode?" downloaded from http://www.etek-inc.com/applications.html, 3 pages (Aug. 14, 2001).

"ChemScan® UV-2150 Process Analyzers," downloaded from http://www.chemscan.com/literature/uv-2150.html, 9 pages (Sep. 13, 2001).

"ChemScan® UV-6101 Process Analyzers," downloaded from http://www.chemscan.com/literature/uv-6101.html, 4 pages (Sep. 13, 2001).

"ChemScan® Application Summary, Ammonia Feed Control (Chloramination)" downloaded from http://www.chemscan.com/applications/101.html, 2 pages (Sep. 13, 2001).

"ChemScan® Application Summary, Chlorination Control" downloaded from http://www.chemscan.com/applications/99.html, 2 pages (Sep. 13, 2001).

"ChemScan® UV-4100 Process Analyzers," downloaded from http://www.chemscan.com/literature/uv-4100.html, 5 pages (Sep. 13, 2001).

"ChemScan® UV-3150 Process Analyzers," downloaded from http://www.chemscan.com/literature/uv-3150.html, 5 pages (Sep. 13, 2001).

"ChemScan® Application Summary, Wastewater Chloramination Process Control" downloaded from http://www.chemscan.com/applications/82.html, 2 pages (Sep. 13, 2001).

"ChemScan® Application Summary, Water Chloramination Process Control" downloaded from http://www.chemscan.com/applications/86.html, 4 pages (Sep. 13, 2001).

"Chlormaines," Gerard J. Gash, OSMONICS, downloaded from http://www.osmonics.com/products/Page813.htm, 5 pages (Sep. 17, 2001).

"A Closer Look At Water Treatment," HACH Company, 1 page (1997).

"Monitoring Chlormaination Using the APA6000 Ammonia/Monochloramine Analyzer," Application Note 123, 6 pages (2000).

"APA 6000 Ammonium & Nitrate Analyzer with AquaTrend Interface," HACH Company, 6 pages (1998).

"Model 1054B CL Chlorine Microprocessor Analyzer," Emerson Process Management, downloaded from http://www.rauniloc.com/1-800-854-8257/01_products_00.php?body=ch_analyzers_1054BCL, 2 pages (Feb. 15, 2002).

"Field Commissioned Dual Measured Analyzer," Emerson Process Management, downloaded from http://www.rauniloc.com/1-800-854-8257/01_products_00.php?body=analyzers_1055FC, 1 page (Feb. 15, 2002).

"Free Chlornie," Emerson Process Management, downloaded from http://www.rauniloc.com/1-800-854-8257/01_products_00.php?body=ch_transmitters_1181RC, 1 page (Feb. 15, 2002).

"Chlorine Measurement by Amperometric Sensor," Application Data, Rosemount Analytical, 1 page (Dec. 1998).

Rosemount Analytical—Uniloc Division launches their 499A TrDO (Trace Dissolved Oxygen) Sensor, 1 page (Mar. 2, 2001).

"APA 6000 Series Analyers: Overview" HACH Company, 5 pages (Sep. 12, 2001).

Copy of International Search Report and Written Opinion from application No.; PCT/US2005/025830, filed Jul. 22, 2005.

* cited by examiner

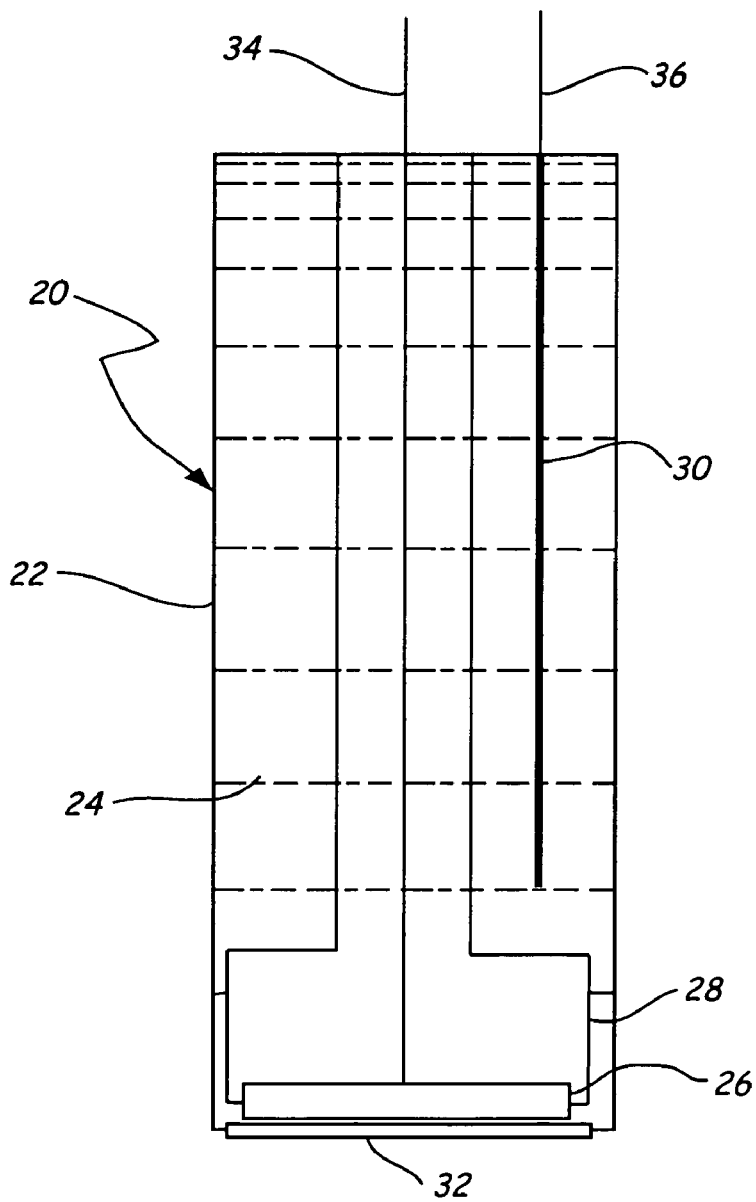
Fig. 2A (SENSOR 20)
(PRIOR ART)

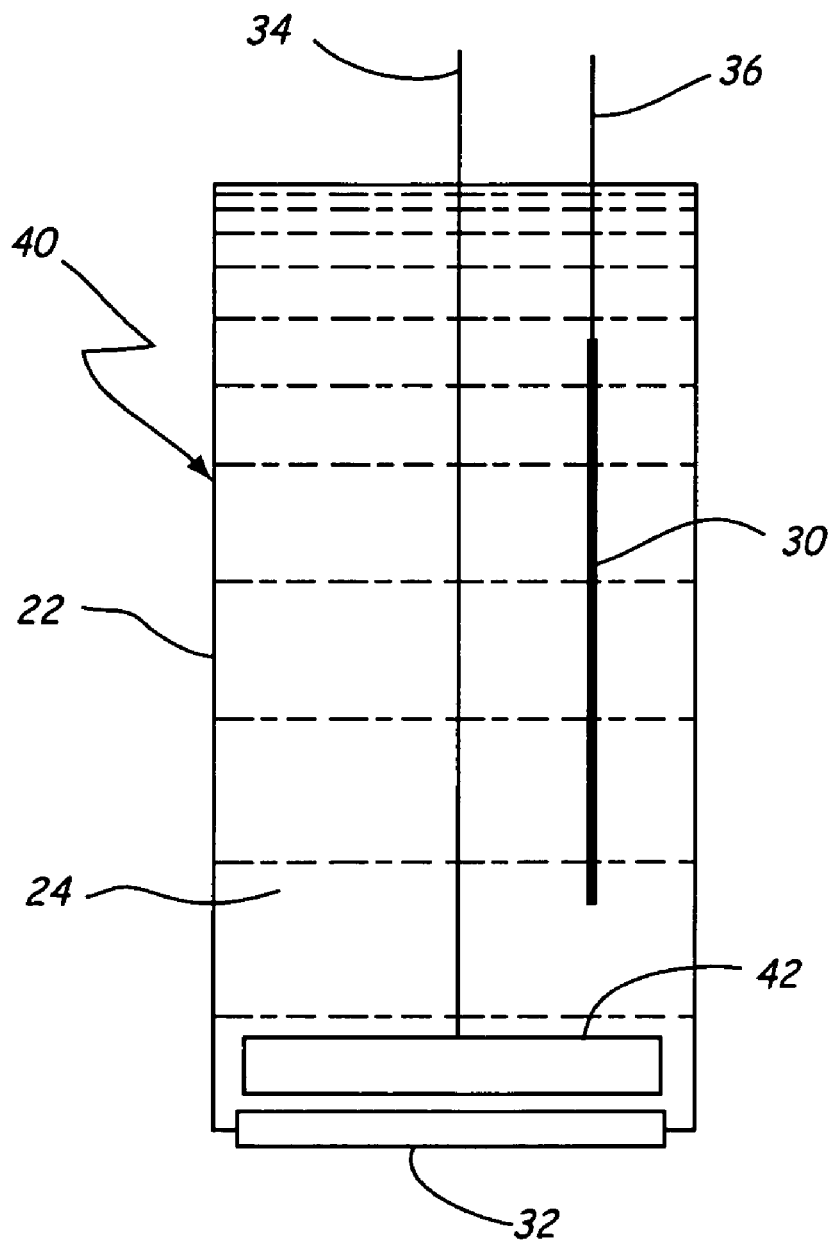
GAS DIFFUSION ELECTRODE
*Fig. 2B* (SENSOR 40)

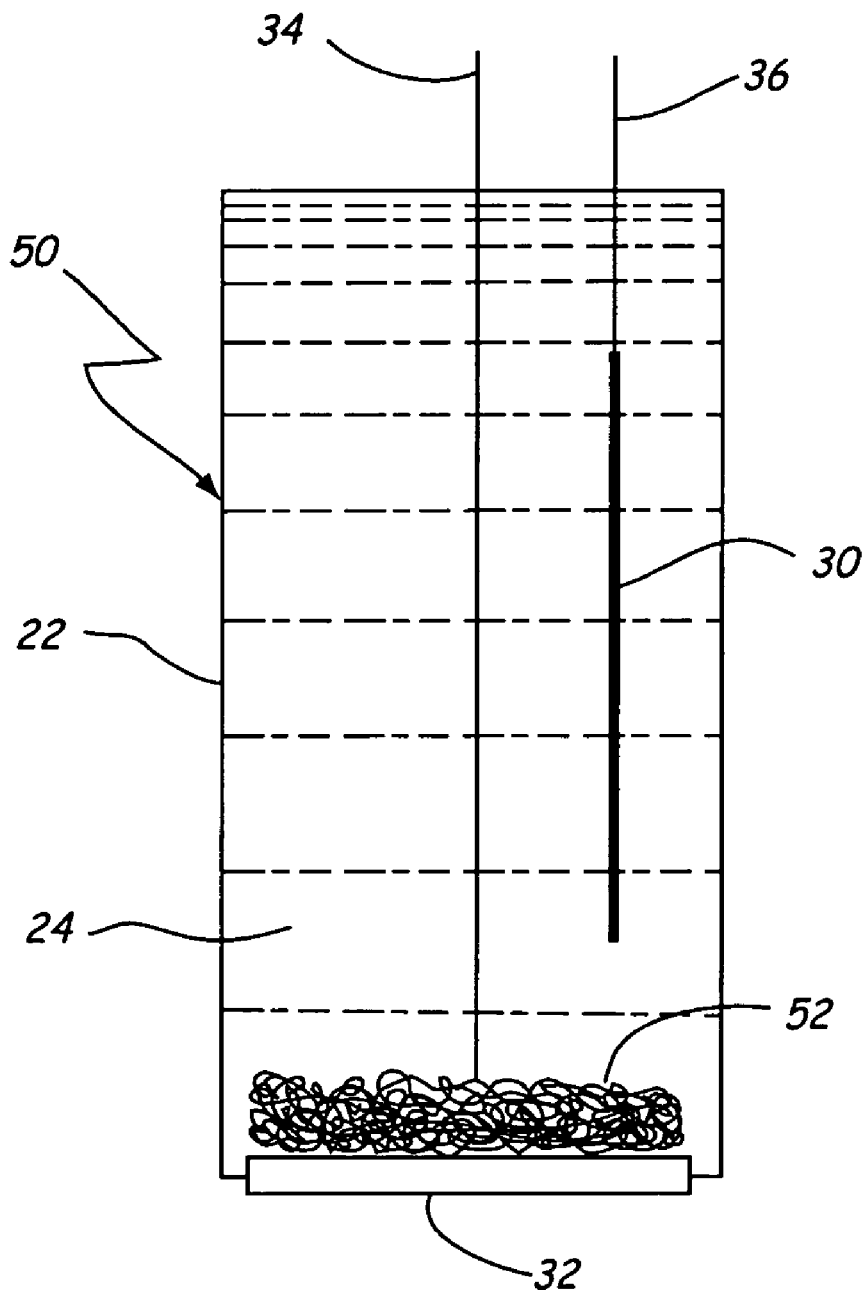
GOLD MESH SENSOR
Fig. 2C  (SENSOR 50)

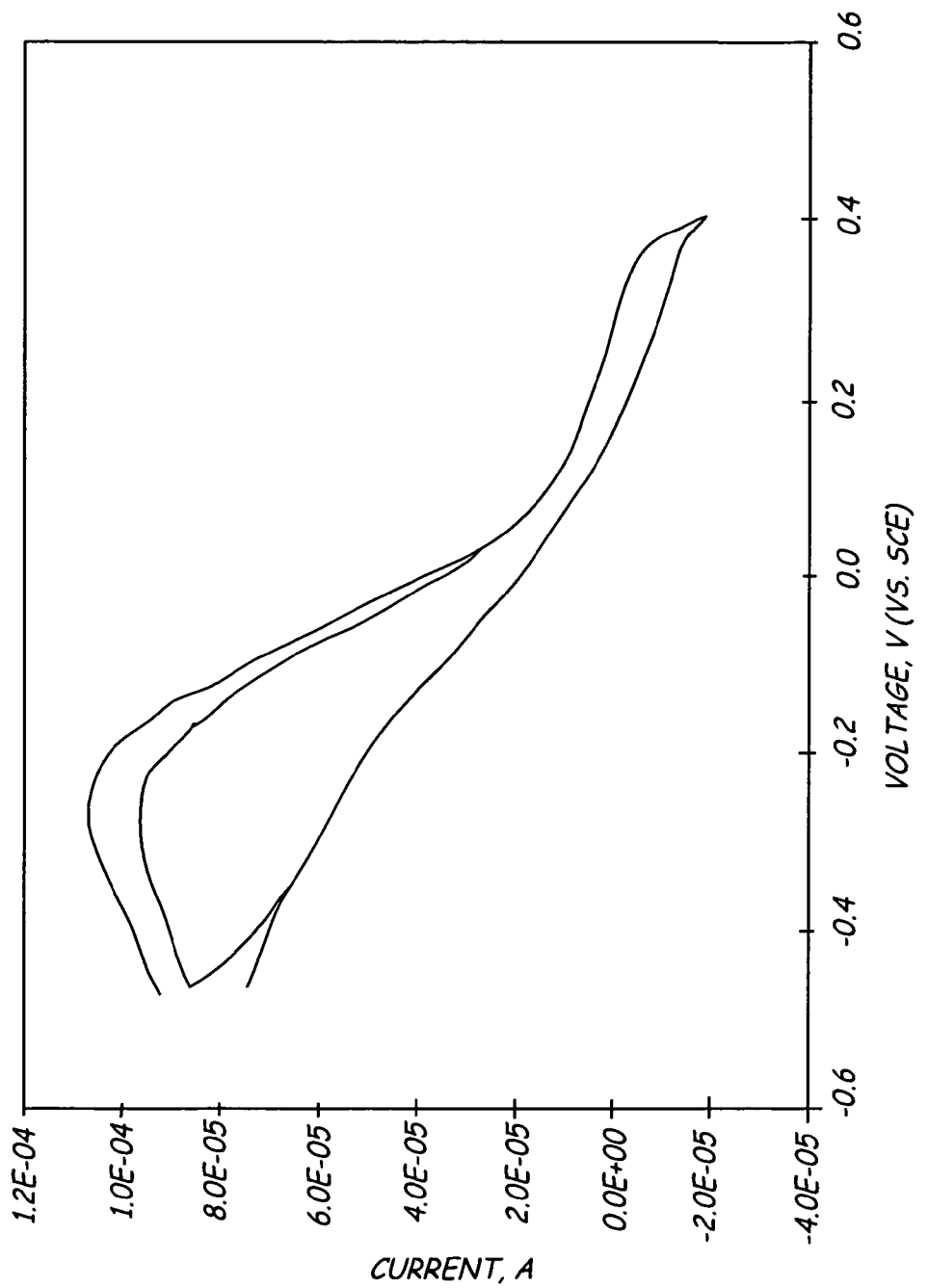
Fig. 3 (SOLID METAL WORKING ELECTRODE)

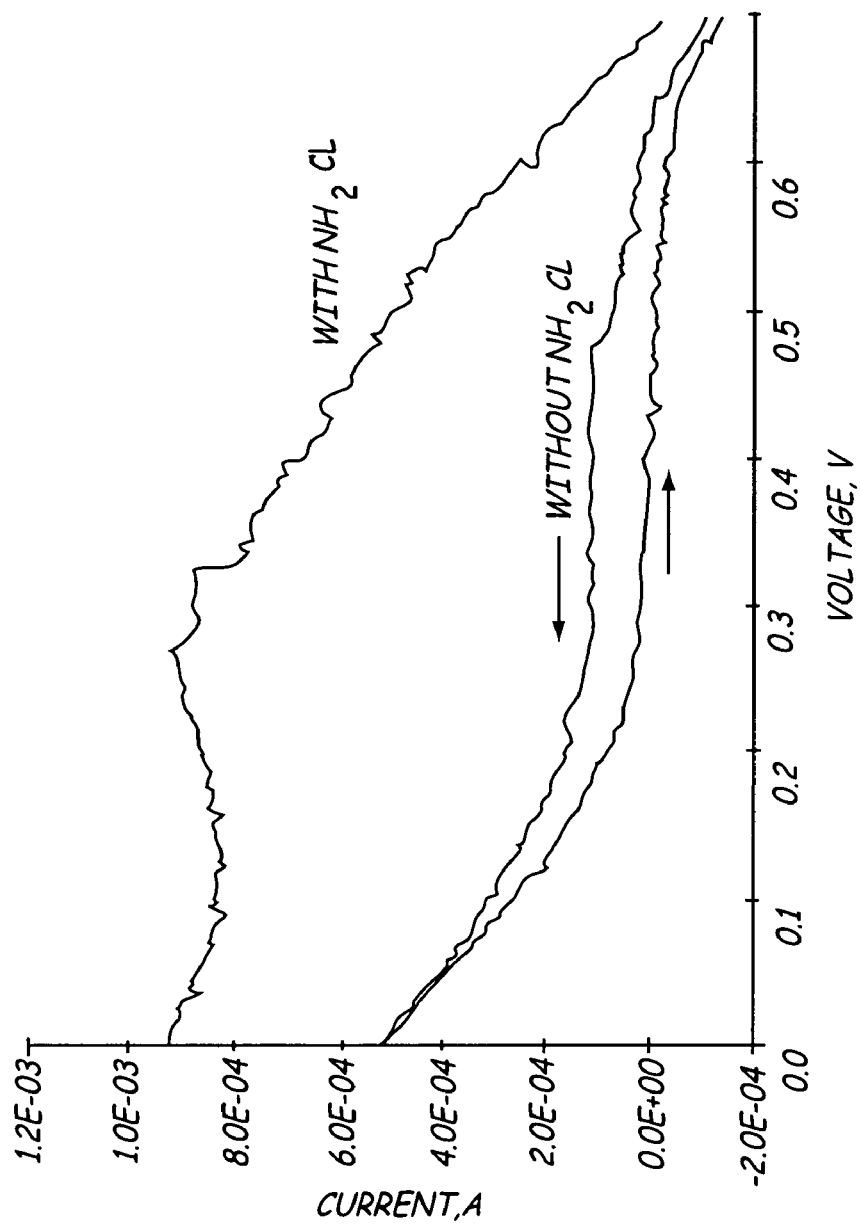
Fig. 4 (GAS DIFFUSION ELECTRODE)

CHLORAMINE AMPEROMETRIC SENSOR

BACKGROUND OF THE INVENTION

The present invention relates to quantitative analytic sensors. More specifically the present invention relates to a sensor that uses an electrode response to measure the concentration of chloramine in a solution.

Chloramine is often used in the treatment of water. While chloramine is generally not as powerful a disinfectant as chlorine, it is often used instead of chlorine because it persists longer and provides a number of other benefits. Thus, sensing chloramine provides useful information for such treatment systems as well as any other system where chloramine is used.

Amperometric sensors are generally known. In such sensors, a species of interest reacts electrically to generate an electrical response that is measured in the form of current flow. One example of a chloramine amperometric sensor is the Model 499A DO-54-99 (SQ6684) available from Emerson Process Management, Rosemount Analytical Division, of Irvine Calif.

Development of embodiments of the present invention is due, at least in part, to a recognition of limitations of current state of the art chloramine amperometric sensors. For example, current sensors generally use a sensing electrode that consists of a solid metallic disc or other shape that is generally a noble metal. The chloramine diffuses across a gas-permeable membrane, such as polytetrafluoroethylene (PTFE) and enters an electrolytic solution. The chloramine then reduces a second species such as $I^-$ into $I_2$. The reduced second species, such as $I_2$, then obtains electrons from the sensing electrode to generate a current that is related to the quantity of chloramine. However, sensor linearity begins to drop off for higher concentrations of chloramine, about 2 ppm. It is believed that conventional sensors limit the access of the second species, such as I– to sensing electrode (cathode) due to the geometry of the sensing electrode. Another problem with current amperometric sensors for chloramine sensing is due to the activity of dissolved oxygen. If oxygen is dissolved in the chloramine containing specimen, the dissolved oxygen will reduce at a level similar to the chloramine, thus "clouding" the measured chloramine response.

SUMMARY OF THE INVENTION

A chloramine amperometric sensor includes a sensor body with an electrolyte disposed inside the sensor body. A membrane is coupled to the sensor body and adapted to pass chloramine therethrough. A reference electrode is disposed in the electrolyte and coupled to a first conductor. A second conductor is coupled to a working electrode that is disposed proximate the membrane. The working electrode is constructed from a noble metal in non-compact form. The non-compact form can be a Gas Diffusion Electrode, which can include metal mesh, carbon paper, carbon cloth, metal/carbon powder loaded on a porous membrane or any combination thereof.

BRIEF DESCRIPTION OF THE DRAWINGS

FIG. 2A is a diagrammatic view of a conventional chloramine amperometric sensor.

FIG. 2B is a diagrammatic view of a chloramine amperometric sensor in accordance with an embodiment of the invention.

FIG. 2C is a diagrammatic view of a chloramine amperometric sensor in accordance with another embodiment of the invention.

FIG. 3 is a graph of the cyclic voltammetry curve of a Platinum electrode in a 100 ppm chloramine solution at pH 7.

FIG. 4 is a graph of a potential scan of a Platinum black loaded Gas Diffusion Electrode (GDE) in a 100 ppm chloramine solution at pH 7 illustrating cyclic voltammetry both in the presence and absence of chloramine.

DETAILED DESCRIPTION OF THE PREFERRED EMBODIMENTS

Embodiments of the present invention provide a chloramine amperometric sensor that employs a working electrode with significantly higher porosity than previous working electrodes. One example includes using a Gas Diffusion Electrode (GDE) loaded with a powdered noble metal catalyst to measure chloramine concentration. Another example includes using a working electrode constructed from noble metal mesh. Amperometric sensors that employ screens on the anode are known. See, for example, U.S. Pat. No. 4,776,942. However, since the screen is used at the counter electrode, it provides no benefit for increasing access to the sensing electrode, where sensing process occurs.

Figure 1:
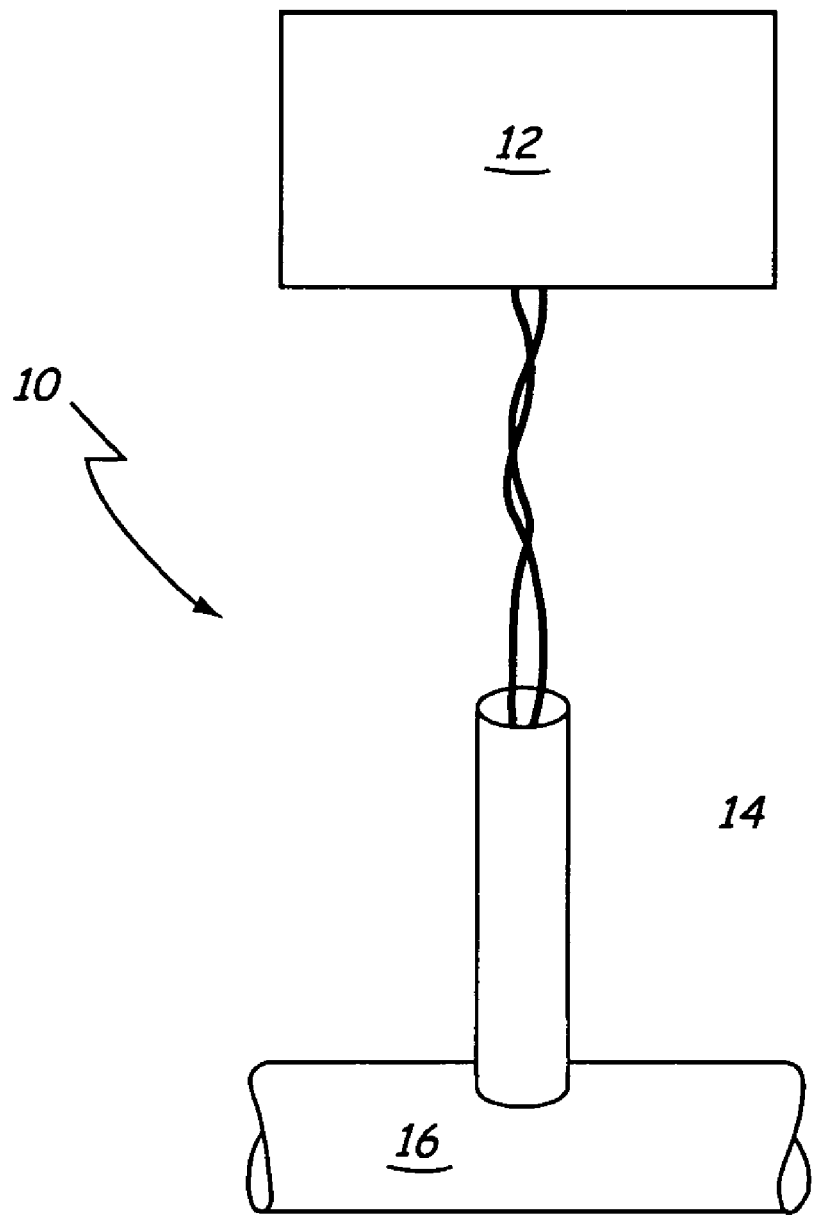
FIG. 1 is a diagrammatic view of a chloramine monitoring system in which embodiments of the present invention are particularly useful.

FIG. 1 is a diagrammatic view of a chloramine monitoring system in which embodiments of the present invention are particularly useful. System 10 includes analysis device 12 and sensor 14. Analysis device 12 can be any suitable device capable of generating meaningful chloramine information from sensor 14. For example, device 12 can be an analyzer such as the Model 1054 Microprocessor Analyzer available from Rosemount Analytical Inc. Uniloc Division of Emerson Process Management. Device 12 can also be a transmitter that is adapted to generate chloramine data and transmit the data over a process communication loop. One example of such a transmitter is the Model 1181RC Transmitter available from Rosemount Analytical Uniloc. Sensor 14 is coupled to sample specimen container 16, which may be a pipe for example. Sensor 14 has an electrical characteristic that varies in response to chloramine concentration in the specimen.

FIG. 2A is a diagrammatic view showing a conventional chloramine amperometric sensor. Sensor 20 generally includes a sensor body 22 that contains a quantity of electrolyte 24. Working electrode 26 (also referred to herein as the cathode, or sensing electrode) is supported within body 22 on support 28 such that it contacts membrane 32. Reference electrode 30 (also referred to as an anode, or counter-electrode) is also disposed within electrolyte 24, but is spaced apart from working electrode 26. Electrode 30 can be any standard reference electrode such as Silver/Silver Chloride. Membrane 32 is disposed at one end of body 22 and is generally placed in contact with the chloramine containing sample. Membrane 32 can be a commercially available porous membrane sold under the trade designation Zitex G106 from Saint-Gobain Ceramics & Plastics, Inc., of Wayne, N.J., but can be any suitable porous material that does not allow the electrolyte to leak from the sensor. Conductors 34 and 36 are coupled to electrodes 26 and 30, respectively, to allow device 12 to measure the electrical characteristic of sensor 20 that varies with chloramine concentration. Working electrode 26 is formed from a solid disc of platinum, but can be any suitable noble metal, such as gold. As such, the only path of the electrolyte to the working electrode is the thin layer between the working electrode and the membrane. This limited contact results in reduced sensor output at high concentrations.

FIG. 2B is a diagrammatic view showing chloramine amperometric sensor 40 in accordance with an embodiment of the invention. Sensor 40 bears some similarities to sensor 20 described with respect to FIG. 2A and like components are numbered similarly. Working electrode 42 is disposed proximate membrane 32. Working electrode 42 provides substantially more accessibility to the electrolyte 24 than working electrode 26. In one preferred embodiment, electrode 42 is a Gas Diffusion Electrode (GDE). In this example, electrode 42 is a GDE loaded with 80 percent platinum-black (powdered platinum) and carbon on a carbon cloth electrode (ECC). The platinum was distributed at a density of about 5.0 mg/cm$^2$. The configuration used for working electrode 26 can be obtained from E-Tek, Inc. (www.etek-inc.com), of Somerset, N.J., USA, by specifying the loading and density listed above. In this embodiment, electrolyte 24 was a pH 10 buffer with potassium chloride (KCl) added as a supporting electrolyte. Preferably, electrolyte 24 has a pH between about 9.0 and 11.0 FIG. 2C is a diagrammatic view of chloramine amperometric sensor 50 in accordance with an embodiment of the present invention. Sensor 50 includes many components that are similar to sensors 20 and 40, and like components are numbered similarly. Sensor 50 includes working electrode 52 constructed from noble metal, in this case gold, in a mesh form. The mesh allows substantially more surface area for electrolyte interaction than a solid working electrode. Working electrode 52 is disposed proximate membrane 32 such that chloramine passing through membrane 32 will interact with both electrolyte and working electrode and generate an electrical response. Those skilled in the art will appreciate that while the platinum black loaded carbon cloth embodiment was described with respect to platinum, and the mesh embodiment was described with respect to gold, embodiments of the present invention can be practiced using any suitable noble metal in either form. Further, it is expressly contemplated that additional forms of presenting the noble metal catalyst to the chloramine are possible as long as they provide a surface area greater than that of a solid. For example, a number of noble metal spheres could be maintained proximate the membrane without departing from the spirit and scope of the invention. As used herein, "non-compact" is intended to mean any form that is not a unitary contiguous solid object.

FIG. 3 is a plot illustrating a Cyclic Voltammetry (CV) curve of the conventional sensor described with respect to FIG. 2A. In FIG. 3, the reduction current peak at about −300 mV arises from the chloramine reduction. The reduction peak is thus in the oxygen reduction potential region. This overlap of chloramine reduction potential with oxygen reduction potential was a significant drawback for prior art amperometric chloramine sensors.

FIG. 4 illustrates a potential scan for sensor 40 described with respect to FIG. 2B. The chart illustrates two runs, one run included testing solution containing chloramine at a concentration of 100 ppm at a pH of 7, while another run was performed in the absence of chloramine. FIG. 4 illustrates sensor response to chloramine, and other free chlorine species. FIG. 4 also illustrates the chloramine reduction potential at the GDE is in a more positive region, compared to FIG. 3, and thus has moved away from the oxygen reduction potential. Thus, it is believed that chloramine sensors in accordance with various embodiments of the invention will not suffer from interference from dissolved oxygen.

Figure 5:
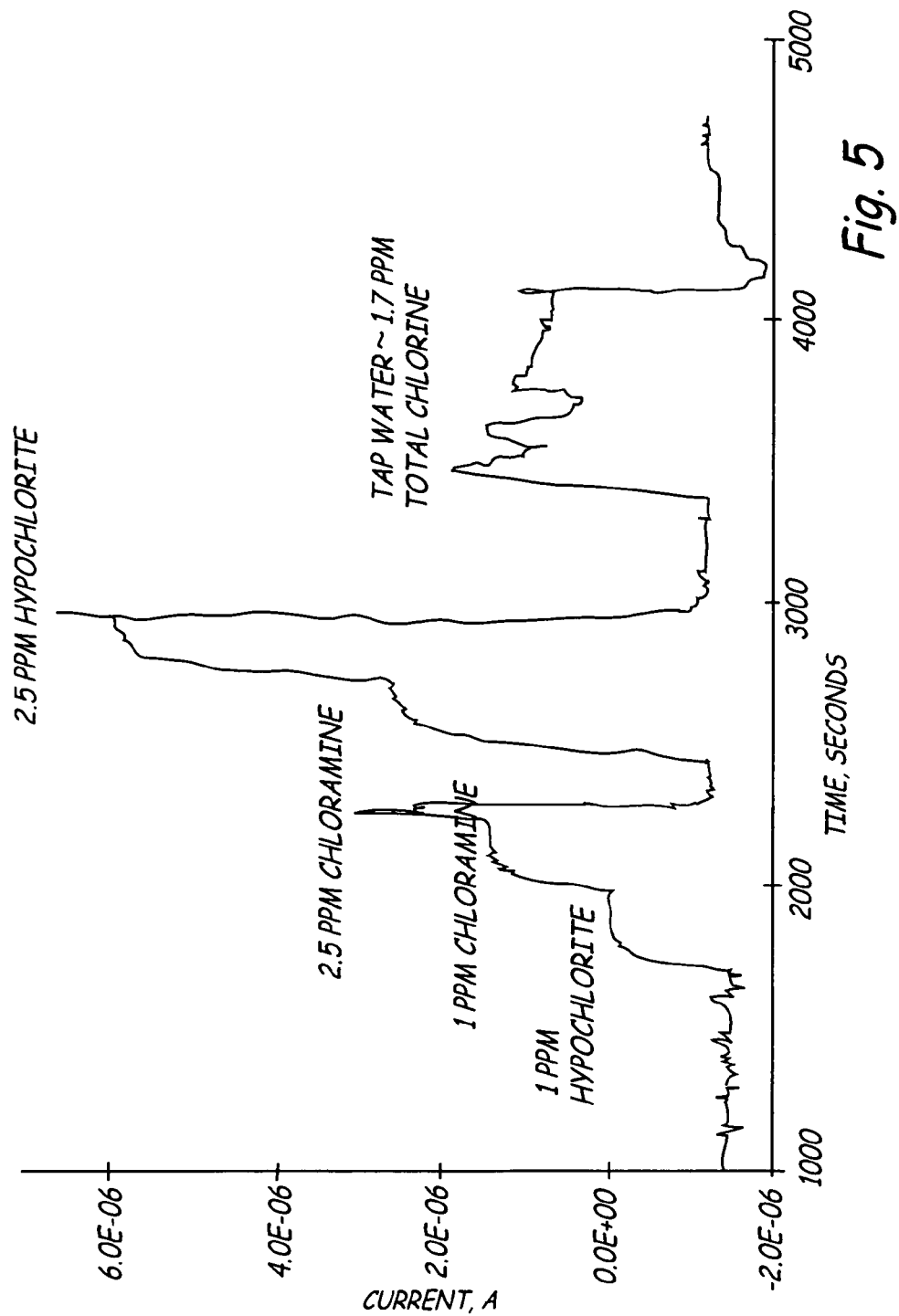
FIG. 5 is a graph of a response curve of a sensor in accordance with an embodiment of the invention to different free chlorine species.

FIG. 5 is a graph of a response curve of sensor 40 to different free chlorine species. The x-axis represents a time period during which sensor 40 was introduced to various testing solutions. When introduced to the various testing solutions, sensor 40 eventually arrived at the following currents:

| | |
|---|---|
| 1 ppm hypochlorite | 0.0E+00; |
| 1 ppm chloramine | 1.5E−06; |
| 2.5 ppm chloramine | 2.8E−06; |
| 2.5 ppm hypochlorite | 6.0E−06; and |
| 1.7 ppm total chlorine (tap water) about | 0.5–2.0E−06. |

Figure 6:
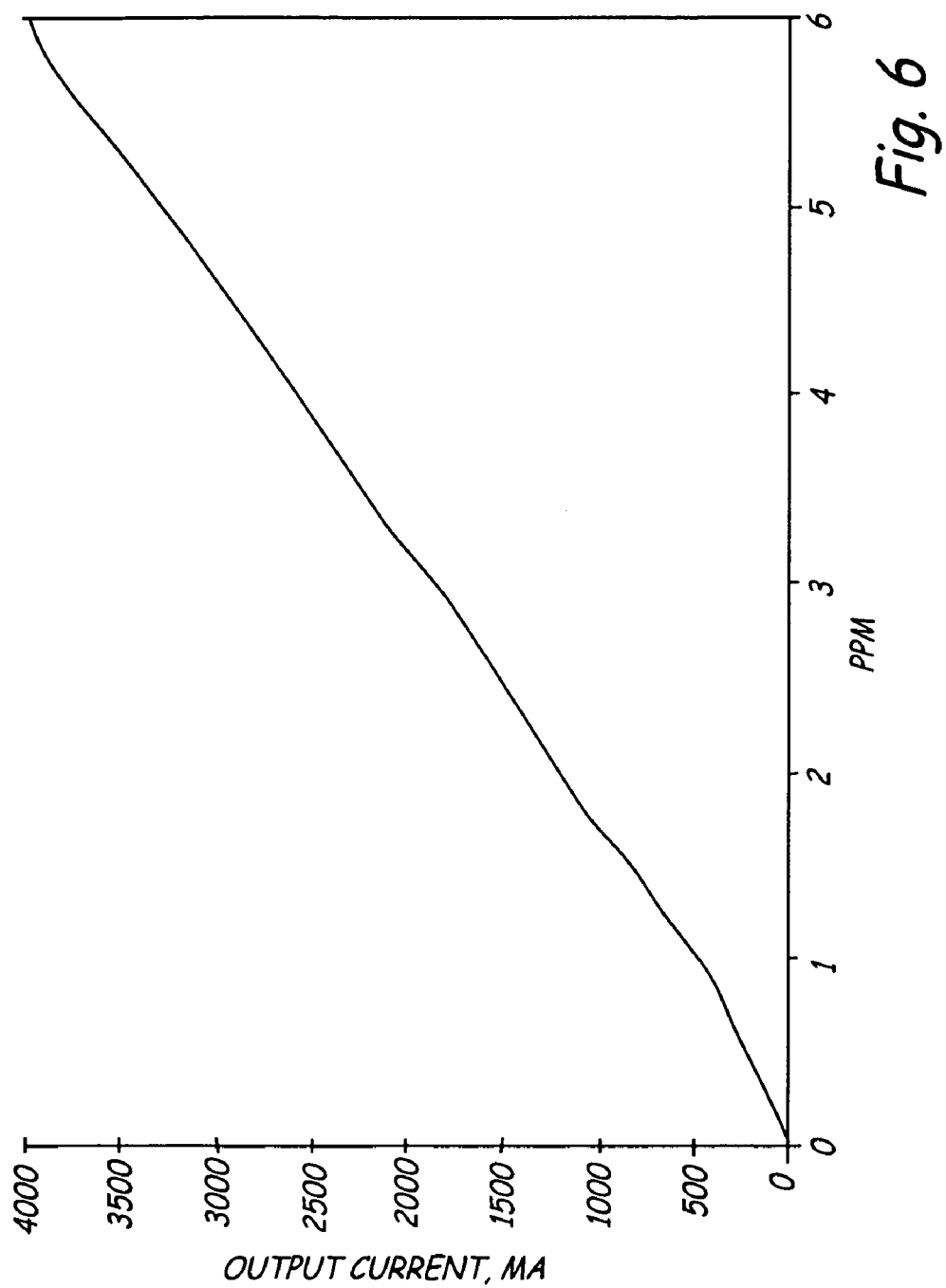
FIG. 6 is a calibration curve illustrating the relationship between output current and chloramine concentration (in the 1.00–8.00 ppm range) for the sensor illustrated in FIG. 2C.

FIG. 6 is a calibration curve illustrating the relationship between output current and chloramine concentration (in the 0–6 ppm range) for sensor 50. As illustrated in FIG. 6, the output current of sensor 50 in response to chloramine concentrations in this range is highly linear. In fact, a linear equation can be fitted to the sensor response to virtually match the sensor response. Thus, a simple linear equation can be used in device 12 to relate sensor output to chloramine concentration. Prior art chloramine sensors are not believed to provide linearity to a concentration near 6 ppm. Thus, it is believed that sensors in accordance with the present invention will provide a predictable linear response in applications where prior art sensor responses would not be linear. Further, due to the enhanced response of sensors in accordance with embodiments of the invention, it is believed that interference from dissolved oxygen in the testing solution is significantly reduced if not eliminated altogether.

Although the present invention has been described with reference to present embodiments, workers skilled in the art will recognize that changes may be made in form and detail without departing from the spirit and scope of the invention.

What is claimed is:

1. In a chemical sensor, a method of measuring chloramine, the method comprising:
    placing a solution containing chloramine in fluidic communication with a membrane permeable to chloramine;
    providing a working electrode having a noble metal in non-compact form, wherein the working electrode at least partially submerged in electrolyte;
    diffusing the chloramine through the membrane into the working electrode;
    measuring a current between the working electrode and a reference electrode disposed in the electrolyte; and
    determining the chloramine from the measured current.

2. The method of claim 1, wherein the sensor comprises a sensor body positionable within the solution containing chloramine.

3. The method of claim 2, wherein the non-compact form is a gas diffusion electrode.

4. The method of claim 3, wherein the gas diffusion electrode is loaded with the noble metal in a powdered form.

5. The method of claim 4, wherein the noble metal is platinum.

6. The method of claim 5, wherein gas diffusion electrode includes carbon cloth and wherein the platinum is loaded onto the gas diffusion electrode at approximately 80% on the carbon cloth.

7. The method of claim 3, wherein the gas diffusion electrode includes a carbon cloth.

8. The method of claim 2, wherein the non-compact form of the working electrode is a mesh.

9. The method of claim 8, wherein the working electrode is constructed from gold mesh.

10. The method of claim 2, wherein the pH of the electrolyte is within the range of about 9.0 to about 11.0.

11. The method of claim 2, wherein the sensor has an output that is linear in concentrations of chloramine ranging from about 0 ppm to about 8.0 ppm.

12. The method of claim 2, wherein the reference electrode is constructed from silver.

13. The method of claim 2, wherein the electrolyte includes potassium chloride.

14. The method of claim 13, wherein the potassium chloride is present at a concentration of about 0.1 M.

15. The method of claim 2, and further comprising:

coupling an analysis device to the reference electrode and the working electrode, the analysis device adapted to provide a sufficient working potential and to measure a current flowing between the reference electrode and working electrode and provide an indication of chloramine concentration in the specimen based on the current.

16. The method of claim 15, and further comprising transmitting data indicative of the concentration with the analysis device.

* * * * *